US009833124B2

(12) United States Patent
Tsuruta et al.

(10) Patent No.: US 9,833,124 B2
(45) Date of Patent: Dec. 5, 2017

(54) TREATMENT TOOL AND ENDOSCOPE SYSTEM WITH INDUCTANCE ELEMENTS TO POWER TREATMENT DEVICE OF TREATMENT TOOL

(71) Applicant: OLYMPUS CORPORATION, Shibuya-ku, Tokyo (JP)

(72) Inventors: Shoei Tsuruta, Tachikawa (JP); Yuta Sugiyama, Hachioji (JP); Akira Matsui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/840,987

(22) Filed: Aug. 31, 2015

(65) Prior Publication Data
US 2015/0366434 A1 Dec. 24, 2015

Related U.S. Application Data

(63) Continuation of application No. PCT/JP2014/052422, filed on Feb. 3, 2014.

(30) Foreign Application Priority Data

Jun. 28, 2013 (JP) ................................ 2013-136762

(51) Int. Cl.
A61B 1/018 (2006.01)
A61B 1/00 (2006.01)
(Continued)

(52) U.S. Cl.
CPC .......... A61B 1/00029 (2013.01); A61B 1/005 (2013.01); A61B 1/00071 (2013.01);
(Continued)

(58) Field of Classification Search
CPC ............ A61B 1/00027; A61B 1/00029; A61B 1/00071; A61B 1/005; A61B 1/018;
(Continued)

(56) References Cited

U.S. PATENT DOCUMENTS 5,052,997 A * 10/1991 Ruggera ................ A61N 1/403
219/748
5,817,092 A * 10/1998 Behl ................... A61B 18/1206
606/1
(Continued)

FOREIGN PATENT DOCUMENTS

CN 102474133 A 5/2012
CN 104321029 A 1/2015
(Continued)

OTHER PUBLICATIONS

International Search Report dated Apr. 28, 2014 with English Language Translation in International Patent Application No. PCT/JP2014/052422, together with English Language Translation.
(Continued)

Primary Examiner — John P Leubecker
(74) Attorney, Agent, or Firm — Scully, Scott, Murphy & Presser, P.C.

(57) ABSTRACT

An endoscope system having: an endoscope having: an endoscope insertion section wherein the endoscope defines a channel having a distal opening in the endoscope insertion section; and a first inductance element arranged to the channel, and configured to receive a high-frequency power to generate an AC magnetic field; and a treatment tool having: a treatment tool insertion section configured to be movably inserted in the channel; an electrically powered treatment device attached to the treatment tool insertion section; and a second inductance element arranged to the treatment tool insertion section, wherein the second inductance element is electrically connected to the electrically
(Continued)

powered treatment device, and wherein the second inductance element is inductively coupled to the first inductance element such that the AC magnetic field induces an electromotive force to generate an induced current in the second inductance element to power the electrically powered treatment device.

18 Claims, 8 Drawing Sheets

(51) Int. Cl.
  A61B 1/005   (2006.01)
  A61B 18/14   (2006.01)
  A61B 18/12   (2006.01)
  A61B 17/00   (2006.01)
  A61B 18/00   (2006.01)
  H02J 50/10   (2016.01)

(52) U.S. Cl.
  CPC .............. *A61B 1/018* (2013.01); *A61B 18/12* (2013.01); *A61B 18/1442* (2013.01); *A61B 18/1492* (2013.01); *A61B 2017/0034* (2013.01); *A61B 2018/00077* (2013.01); *A61B 2018/00178* (2013.01); *A61B 2018/00982* (2013.01); *A61B 2560/0214* (2013.01); *H02J 50/10* (2016.02)

(58) Field of Classification Search
  CPC ........... A61B 2018/00077; A61B 2018/00178; A61B 2018/00982; A61B 2560/0204; A61B 2560/0214; A61B 2017/0034
  See application file for complete search history.

(56) References Cited

U.S. PATENT DOCUMENTS

| | | | | |
|---|---|---|---|---|
| 5,849,020 A * | 12/1998 | Long | .................. | A61B 18/1447 606/167 |
| 5,916,215 A * | 6/1999 | Long | .................. | A61B 18/1487 606/41 |
| 6,206,875 B1 * | 3/2001 | Long | .................. | A61B 18/1487 128/898 |
| 6,371,967 B1 * | 4/2002 | Long | .................. | A61B 18/1447 606/167 |
| 6,949,068 B2 | 9/2005 | Taniguchi et al. | | |
| 7,824,407 B2 | 11/2010 | Yamamoto et al. | | |
| 8,854,216 B2 | 10/2014 | Uchida | | |
| 2001/0020167 A1 * | 9/2001 | Woloszko | .......... | A61B 18/1402 606/45 |
| 2004/0116952 A1 | 6/2004 | Sakurai et al. | | |
| 2004/0133189 A1 | 7/2004 | Sakurai | | |
| 2008/0015409 A1 * | 1/2008 | Barlow | .............. | A61B 18/1492 600/106 |
| 2010/0179384 A1 * | 7/2010 | Hoeg | .................. | A61B 1/00016 600/109 |
| 2010/0191238 A1 * | 7/2010 | Kornerup | ........... | A61B 18/1206 606/47 |
| 2010/0249600 A1 | 9/2010 | Kudoh et al. | | |
| 2011/0018359 A1 * | 1/2011 | Wada | .................... | B60L 11/182 307/104 |
| 2011/0160514 A1 | 6/2011 | Long et al. | | |
| 2011/0251606 A1 * | 10/2011 | Kerr | .................... | A61B 18/1402 606/34 |
| 2012/0116380 A1 * | 5/2012 | Madan | ............. | A61B 17/00234 606/33 |
| 2012/0184951 A1 * | 7/2012 | Viola | ................ | A61B 17/00234 606/34 |
| 2015/0057653 A1 | 2/2015 | Sugiyama | | |
| 2015/0333535 A1 * | 11/2015 | Feine | ..................... | A61C 17/20 307/104 |

FOREIGN PATENT DOCUMENTS

| | | |
|---|---|---|
| EP | 0 894 476 A1 | 2/1999 |
| EP | 2 865 348 A1 | 4/2015 |
| JP | H11-128242 A | 5/1999 |
| JP | 2000-217826 A | 8/2000 |
| JP | 2000-254134 A | 9/2000 |
| JP | 2000-254141 A | 9/2000 |
| JP | 2000-287987 A | 10/2000 |
| JP | 2002-165388 A | 6/2002 |
| JP | 2002-325721 A | 11/2002 |
| JP | 2004-208922 A | 7/2004 |
| JP | 2007-117405 A | 5/2007 |
| JP | 2011-030317 A | 2/2011 |
| JP | 2014-004237 A | 1/2014 |
| WO | 2013/177006 A2 | 11/2013 |

OTHER PUBLICATIONS

International Search Report dated Aug. 6, 2013 with English Language Translation, and Written Opinion of the International Search Authority with English Translation in International Patent Application No. PCT/JP2013/066735.

Extended Supplementary European Search Report dated Jan. 26, 2017 in European Patent Application No. 14 81 74 50.1.

\* cited by examiner

TREATMENT TOOL AND ENDOSCOPE SYSTEM WITH INDUCTANCE ELEMENTS TO POWER TREATMENT DEVICE OF TREATMENT TOOL

CROSS REFERENCE TO RELATED APPLICATION

This application is a continuation of PCT International Application No. PCT/JP2014/052422, filed on Feb. 3, 2014, the entire content of which is incorporated by this reference, and claims priority to Japanese Patent Application No. JP2013-136762, filed on Jun. 28, 2013, the entire content of which is incorporated by this reference.

BACKGROUND

The present invention relates to an endoscope system for feeding power wirelessly to a device passing through a channel of a flexible endoscope.

U.S. Pat. No. 7,824,407 discloses high-frequency incision forceps for applying high-frequency current to a body tissue to do a treatment as a device passing through a channel of a flexible endoscope and inserted into a body.

Further, U.S. Pat. No. 6,949,068 discloses such an endoscope shape detector that passes a probe comprising multiple magnetism generating elements through a channel to detect and display the shape of a flexible insertion section of an endoscope.

A cable is connected to devices, such as the high-frequency incision forceps, the probe, and the like to supply power necessary for operation. This cable may disturb operator's operations and hence reduce operability.

U.S. Pat. No. 6,371,967 discloses that power is wirelessly fed from a transmission coil of a trocar to a reception coil of an electrosurgical treatment tool inserted in the trocar.

SUMMARY

An endoscope system is provided. The endoscope system comprises: an endoscope comprising: an endoscope insertion section comprising a portion that is flexible, wherein the endoscope defines a channel having a distal opening in the endoscope insertion section; and a first inductance element arranged to the channel, wherein the first inductance element is configured to receive a high-frequency power from a power source to generate an AC magnetic field; and a treatment tool comprising: a treatment tool insertion section configured to be movably inserted in the channel of the endoscope; an electrically powered treatment device attached to the treatment tool insertion section to be moved by the treatment tool insertion section; and a second inductance element arranged to the treatment tool insertion section, wherein the second inductance element is electrically connected to the electrically powered treatment device, and wherein the second inductance element is inductively coupled to the first inductance element such that the AC magnetic field induces an electromotive force to generate an induced current in the second inductance element to power the electrically powered treatment device to perform a treatment.

It is an object of embodiments of the present invention to provide an endoscope system comprising a highly operable device inserted into a channel of a flexible endoscope.

DETAILED DESCRIPTION

First Embodiment

Figure 1:
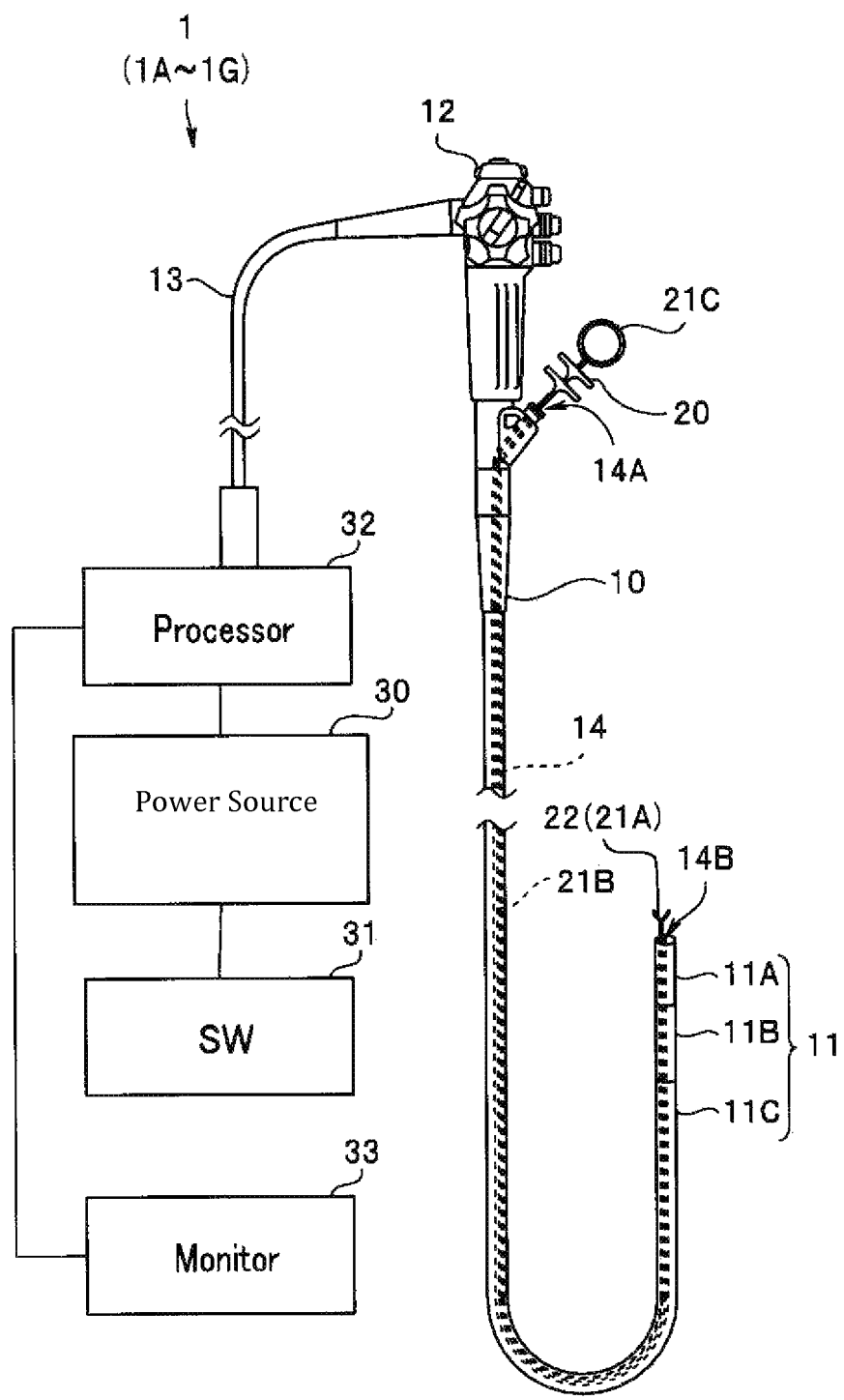
FIG. 1 is a configuration diagram of an endoscope system of a first embodiment.

As illustrated in FIG. 1, an endoscope system 1 of the embodiment comprises a flexible endoscope (hereinafter called "endoscope") 10, a treatment tool 20 as a device passing through a channel 14 of the endoscope 10, and a power source 30.

The endoscope 10 comprises an endoscope insertion section 11 and an operation section 12 arranged on a base end side of the endoscope insertion section 11, and a universal cord 13 provided to extend from the operation section 12. The endoscope insertion section 11 comprises a distal end portion 11A in which an imaging unit 15 (for example, an image sensor such as a CCD or a CMOS) (see FIG. 2) is arranged, a curved portion 11B for changing the direction of the distal end portion 11A, and a soft portion 11C being flexible and elongated. The operation section 12 is a non-flexible section grasped by an operator to perform a directional operation of the distal end portion 11A, an air supply operation, a water supply operation, an endoscopic image taking operation, and the like. On the other hand, the endoscope insertion section 11 is a flexible section to be movably inserted from the oral cavity or the anus of a patient as an object to be treated into an alimentary tract.

A processor 32 as a hardware connected to the universal cord 13 of the endoscope 10 comprises a control unit (not illustrated) composed of a CPU and the like for controlling the entire endoscope system 1 to process an imaging signal output from the imaging unit 15 and display an endoscopic image on a monitor 33. The power source 30 connected to the processor 32 supplies high-frequency power to the treatment tool 20. For example, a foot switch SW 31 controls ON/OFF of the output of the power source 30. Note that a line branched from the universal cord 13 may be connected directly to the power source 30.

The endoscope 10 comprises a channel 14 made of a flexible resin tube passing through the endoscope insertion section 11 from an insertion opening 14A of the operation section 12 to a distal opening 14B of the distal end portion 11A.

The treatment tool 20 comprises a distal end portion 21A in which a treatment unit 22 is arranged, a treatment tool insertion section 21B that is elongated and flexible, and an operation section 21C arranged on the base end side of the treatment tool insertion section 21B and operated by the operator outside the body. The treatment tool 20 is inserted from the insertion opening 14A to pass through the channel 14 and protrude the distal end portion 21A from the distal opening 14B.

The distal end portion 21A comprises a pair of blades (electrodes) 22A, 22B (see FIG. 3) as the treatment unit 22 through which high-frequency current is passed. A body tissue (affected area) LT as a treated area grasped with the pair of blades 22A, 22B (see FIG. 3) of forceps according to the operation in the operation section 21C is excised and bleeding is stopped by Joule heat generated by the high-frequency current.

The power source 30 outputs high-frequency power, for example, with a frequency of not less than 100 kHz and not more than 100 MHz. The frequency of the high-frequency power is preferably selected from frequencies allowed by the laws and the like, which is 13.56 MHz, for example. It is preferred, but not particularly limited to, that the waveform amplitude of the high-frequency power be of a sinusoidal wave.

In the endoscope system 1, the treatment tool 20 and the power source 30 are not connected by wire. However, when the treatment tool 20 is inserted into the channel 14, the treatment tool 20 receives, in wireless power transmission, power required to do a treatment from the power source 30 through the endoscope 10. Note that the wireless power transmission is the same in meaning as wireless power supply.

Figure 2:
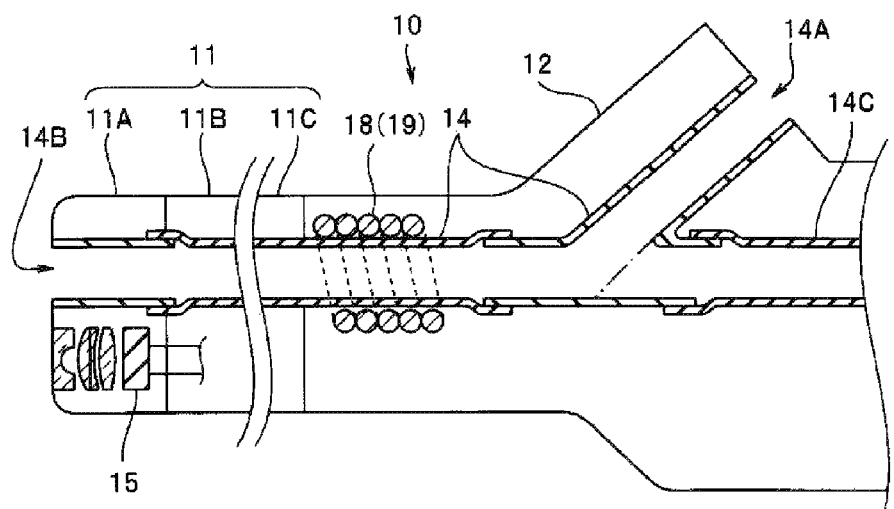
FIG. 2 is a schematic sectional view of an endoscope in the endoscope system of the first embodiment.
Figure 4:
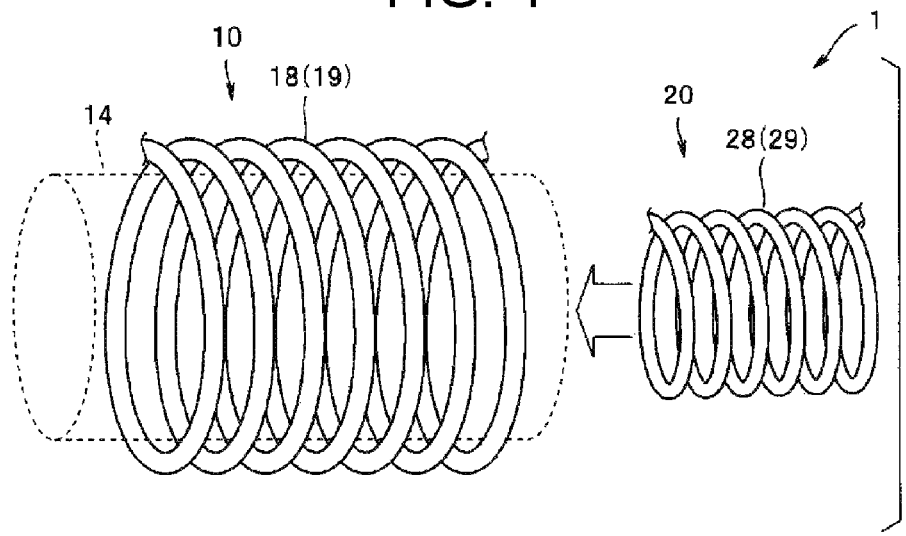
FIG. 4 is a schematic diagram of a transmission coil and a reception coil in the endoscope system of the first embodiment.

In other words, as illustrated in FIG. 2 and FIG. 4, the endoscope 10 comprises a power transmission unit 19 comprising a first inductance element for generating a magnetic field to convert the high-frequency power output from the power source 30 into an AC magnetic field. The first inductance element of the endoscope 10 is a first solenoid coil (hereinafter also called "first coil" or "transmission coil") 18 wound around the outer circumference of the channel 14. Note that the channel 14 comprises a flexible tube and a branch tube, and one side of the branch tube is connected to an air sending and sucking tube 14C.

The power transmission unit 19 may be structured to comprise a hollow section with which part of the channel 14 is replaced as long as it is located inside of at least either the operation section 12 or the endoscope insertion section 11. In other words, in this specification, a component that forms the hollow section in the above structure is also regarded as part of the channel 14. In other words, in this specification, a component that forms the hollow section in the above structure is also regarded as part of the channel 14.

Although the conductor of the first coil 18 may be exposed to the inner surface of the hollow section in terms of the function as an inductance element, it is preferred that the inner surface of the hollow section be sealed by an insulating material with small friction because the channel 14 is also used for sending and sucking air, and the like.

Figure 3:
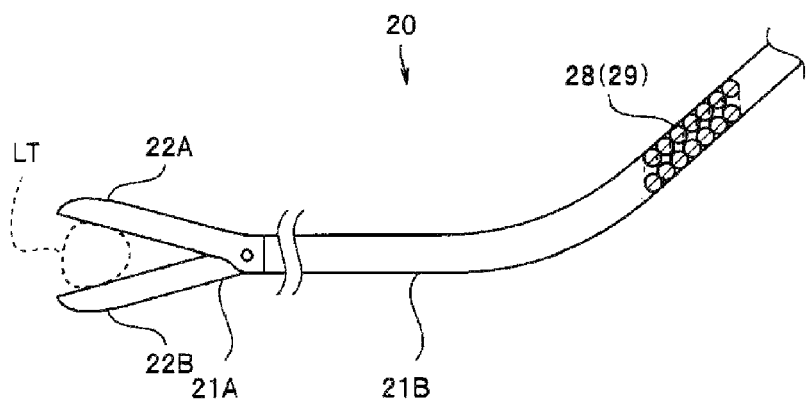
FIG. 3 is a schematic sectional view of a treatment tool in the endoscope system of the first embodiment.

On the other hand, as illustrated in FIG. 3 and FIG. 4, the treatment tool 20 comprises a power reception unit 29 comprising a second inductance element for receiving a magnetic field. The second inductance element of the treatment tool 20 is a second solenoid coil (hereinafter also called "second coil" or "reception coil") 28 wound around in the longitudinal direction of the treatment tool insertion section 21B.

Although the solenoid coils illustrated in FIG. 2 to FIG. 4 are so-called single-layer windings, they may be multi-layer windings such as double layer windings. Further, when the conducting wires of the coils are insulated conducting wires covered with insulating materials, the coils may be wound around more densely so that adjacent conducting wires will come into contact with each other. Since a solenoid coil having a larger number of turns has higher inductance L, it can generate a stronger AC magnetic field and receive higher induced current.

The inner diameter $\phi$ (14) of the channel 14 is larger than the outer diameter $\phi$ (20) of the treatment tool insertion section 21B so that the treatment tool insertion section 21B of the treatment tool 20 can be inserted. For example, $\phi$ (14)=2.8 mm and $\phi$ (20)=2.5 mm.

Note that a region of part of the treatment tool insertion section 21B, where the second coil 28 is arranged, is so arranged that the conductor will not be exposed to the outermost circumferential surface, and if it can be inserted into the channel 14, the outer diameter $\phi$ (20) of the region may be made larger than other regions. Further, it is more preferred that the outer surface of the treatment tool insertion section 21B should be covered with an insulating material with small friction, such as fluorocarbon resin, to make it easy to pass through the channel 14.

As described above, the endoscope system 1 comprises the endoscope 10, the treatment tool 20 for doing a treatment with the treatment unit 22, and the power source 30 for supplying power to the treatment unit 22, wherein the endoscope 10 comprises the flexible endoscope insertion section 11 and the operation section 12 arranged on the base end side of the insertion section, and comprises the channel 14 penetrating through from the treatment tool inserting opening 14A as a based point provided in the operation section 12 to the distal end of the insertion section, and the power transmission unit 19 comprising the transmission coil 18 for generating an AC magnetic field to be applied to the inside of the channel 14, and the treatment tool 20 comprises the power reception unit 29 comprising the reception coil 28 removably passing through the channel 14 from the treatment tool inserting opening 14A, capable of inductively coupled to the AC magnetic field generated in the transmission coil 18, and provided to replace part of the exterior or the interior, and when the treatment tool 20 is inserted into the channel 14, the transmission coil 18 and the reception coil 28 are inductively coupled to each other.

Figure 5A:
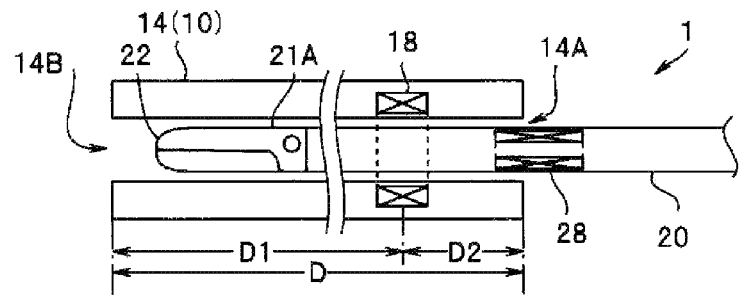
FIG. 5A is a schematic sectional view of the endoscope system of the first embodiment.

Here, as illustrated in FIG. 5A, even when the treatment tool 20 is inserted into the channel 14 from the insertion opening 14A, the second coil 28 of the treatment tool 20 cannot efficiently receive the AC magnetic field generated by the first coil 18 of the endoscope 10 until the distal end portion 21A of the treatment tool protrudes from the distal opening 14B. This is because the AC magnetic field is a non-radiative field that is not propagated in the same way as electric waves. In other words, for example, the wavelength of the AC magnetic field is about 22 m at a frequency of 13.56 MHz, while the structure is sufficiently small compared therewith. Thus, the AC magnetic field is not propagated to a long distance like the electric waves.

Figure 5B:
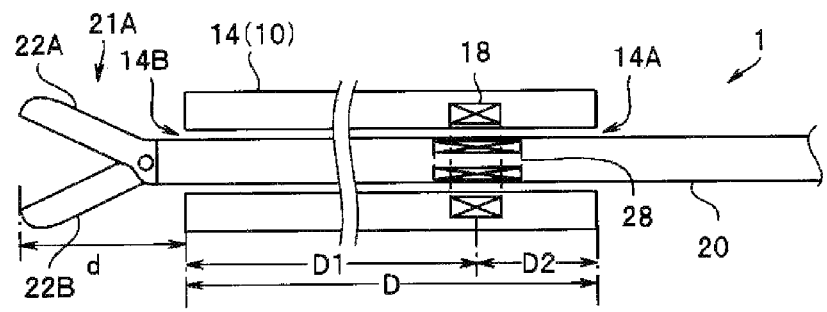
FIG. 5B is a schematic sectional view of the endoscope system of the first embodiment.

On the other hand, in a state where the distal end portion 21A of the treatment tool is protruding from the distal opening 14B, i.e., a state where the treatment tool 20 is inserted into the channel 14 up to the operating position as illustrated in FIG. 5B, the second coil 28 is inserted inside the first coil 18 in the endoscope system 1, the central axis of the first coil 18 substantially coincides with the central axis of the second coil 28 to become coaxial. Therefore, even when the position of the treatment tool 20 inside the channel 14 is made eccentric from the center of the channel 14, power transmission/reception efficiency (transmission efficiency) does not greatly vary. The first coil 18 and the second coil 28 are inductively coupled stably. Thus, the second coil 28 can receive the AC magnetic field generated by the first coil 18 most efficiently by the electromagnetic induction effect.

Here, it is preferred that the length of the first coil 18 and the second coil 28 be 1 cm or more. If the length is in the above range or more, power can be transmitted and received. On the other hand, the maximum length of the first coil 18 is determined by a length D of the channel 14, and the maximum length of the second coil 28 is determined by the length of the treatment tool insertion section 21B. For example, the channel length D of the flexible endoscope 10 and the length of the treatment tool insertion section 21B are about not less than 100 cm and not more than 230 cm, and the maximum length of the first coil 18 and the second coil 28 is the same as the channel length D. Note that it is particularly preferred that the length of the first coil 18 and the second coil 28 be not less than 5 cm and not more than 200 cm in terms of the transmission/reception efficiency and the self-inductance.

Although the first coil 18 illustrated in FIG. 2 is arranged around the channel 14 in the operation section 12, the first coil 18 may be arranged around the channel 14 in the soft portion 11C, or arranged around the channel 14 in the operation section 12 and the soft portion 11C. Further, the length of the second coil 28 illustrated in FIG. 3 is short, but the second coil 28 may be a coil having substantially the same length as the length of the treatment tool insertion section 21B, for example.

Although the length D of the channel 14 of the endoscope 10 is very long as 100 cm or more, most of the length is placed inside the flexible, soft portion 11C. Therefore, although it is easy to set the length of the first coil 18 and the second coil 28 to 50 cm or more, the first coil 18 and the second coil 28 placed inside the flexible, soft portion 11C need to be flexible.

The endoscope system 1 comprising the flexible endoscope 10 comprising the endoscope insertion section 11 that is flexible and elongated is high in the efficiency of wireless power transmission because it can increase the length of the first coil 18 and the second coil 28 according to the length of the endoscope insertion section 11, for example, to 50 cm or more. Note that the upper limit of the length of the first coil 18 and the second coil 28 is, for example, 200 cm.

Here, the longer the coil, the higher the resistance R. Therefore, in light of the transmission efficiency depending on a Q value proportional to inductance L/resistance R, it is particularly preferred that the coil length should be 200 cm or less in the case of the single-layer winding and 150 cm or less in the case of the double layer winding.

A state where the transmission/reception efficiency becomes the highest is a state where the coaxial second coil 28 is inserted into the entire length of the first coil 18, i.e., a state where the second coil 28 penetrates through the first coil 18. Therefore, it is preferred that the length of the second coil 28 be longer than the length of the first coil 18, and in light of the protrusion amount d from the distal opening 14B of the treatment tool 20, it is particularly preferred that the length of the second coil 28 be (length of the first coil 18+protrusion amount d). Note that the protrusion amount d is, for example, not less than 1 cm and not more than 10 cm, though it depends on the treatment tool.

Here, it is preferred that the same treatment tool 20 can be used even for multiple endoscopes different in channel length D. To this end, it is preferred that the arrangement position of the first coil 18 should be set with reference to the distal opening 14B. In other words, the first coil 18 of the endoscope only needs to be arranged in a position a predetermined distance D1 from the distal opening 14B. In this case, distance D2 from the insertion opening 14A to the first coil 18 in an endoscope having a longer channel length D becomes longer than that of an endoscope having a shorter channel length D.

In an endoscope system comprising multiple endoscopes, in each of which the first coil 18 is arranged in a position a predetermined distance D1 from the distal opening 14B, and the treatment tool 20, the multiple endoscopes can wirelessly feed power to the treatment tool 20 efficiently.

It goes without saying that an endoscope system comprising one endoscope and multiple treatment tools has the same effect, where the power reception unit 29 is arranged in a position of receiving the alternating electric field generated by the power transmission unit 19 most efficiently in a state of inserting each of the treatment tools into the channel 14 up to the operating position, respectively.

Figure 6:
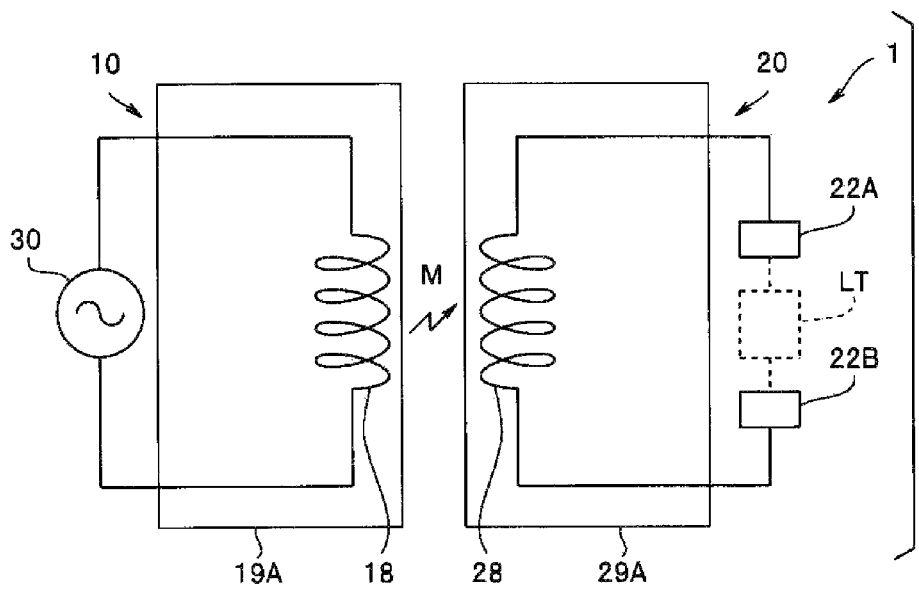
FIG. 6 is an equivalent circuit diagram of the endoscope system of the first embodiment.

In an endoscope system 1, as illustrated in an equivalent circuit diagram of FIG. 6, an endoscope side circuit comprising a power source 30 and a power transmission unit 19 has no physical contact through a conductor with a treatment tool side circuit comprising a power reception unit 29 and treatment units 22 (22A, 22B) to apply current to a body tissue LT as a load section that consumes power.

However, the power reception unit 29 is inductively coupled to a non-radiative AC magnetic field M generated in a space near the power transmission unit 19. An induced electromotive force is generated in the power reception unit 29 inductively coupled, and power generated thereby is supplied to the treatment unit 22 of the treatment tool 20 with an induced current generated by the induced electromotive force. Note that wiring for connection between the power source 30 and the solenoid coil 18 may be ground connection.

Since the treatment tool 20 in the endoscope system 1 has no wiring (cable) connected to the power source 30, it is easy to handle the treatment tool 20 with good operability. Further, since the power transmission unit 19 is arranged inside the endoscope 10, a generated electromagnetic field M is less likely to leak outside the endoscope 10, and the influence of the leakage electromagnetic field on peripheral devices is small.

Further, since the solenoid coil 28 of the treatment tool 20 inserted in the channel 14 is coaxial with the solenoid coil 18 of the endoscope 10, the coupling coefficient is large. In addition, since the length of the solenoid coil 28 and the solenoid coil 18 can be increased up to a length equivalent to that of the endoscope insertion section 11 of the flexible endoscope 10, it is easy to further increase mutual inductance.

A so-called densely wound spiral coil with adjacent element wires being substantially in contact with each other may be arranged in the treatment tool insertion section 21B of the treatment tool 20 to ensure flexibility and mechanical strength. In this case, the solenoid coil 28 can be formed by using part of a shape holding spiral coil of the treatment tool 20 to reduce the size and cost of the treatment tool 20.

In other words, two conducting wires for energization are connected to the shape holding spiral coil so that the field between the conducting wires can be used as the solenoid coil 28. Of course, parts of the element wires used as the solenoid coil 28 are coated with an insulating material to prevent adjacent element wires from being short-circuited. When the shape holding spiral coil is made of stainless steel or the like comprising a relatively high electric resistance, it is preferred that a low-resistance metal material should be formed on the surface by plating with copper, silver, or the like to reduce the electric resistance. Alternatively, at least part of the stainless coil may be replaced by a coil made of a low-resistance metal material so that it will be used as the solenoid coil 28.

Further, since a relative positional relationship between the power transmission unit 19 and the power reception unit 29 is defined by arranging the power transmission unit 19 inside the endoscope 10, the state of strong coupling between the power transmission unit 19 and the power reception unit 29, i.e., a state of high power transmission efficiency can be maintained stably, and energy saving performance is excellent as well.

Here, in the endoscope system 1, the switch 31 is used to control ON/OFF of the power output to the treatment tool 20 as already described above. The switch 31 is illustrated as the foot switch in FIG. 1, but the switch may be arranged in the power source 30, the operation section 12 of the endoscope 10, or the operation section 21C of the treatment tool 20.

The switch connected to the power source 30 or the switch arranged in the power source 30 controls ON/OFF of the output of the power source 30. The switch arranged in the operation section 12 or the operation section 21C controls ON/OFF of power through an internal circuit of the power transmission unit 19 or the power reception unit 29. Instead of the ON/OFF control in the power transmission/reception circuit, a Q value of the power transmission/reception circuit can be increased/decreased to make a vast change in transmission/reception efficiency in order to obtain the same effect as the ON/OFF control. However, when the amount of power is large, the control of decreasing the Q value may cause a problem such as heat generation.

Note that the switch may be a button switch, a touch gesture-capable operating part, a speech-recognition operating part, or the like.

As described above, in the endoscope system 1, the switch as power transmission starting/stopping means for starting or stopping output from the power source 30 is arranged separately from the power source 30, or arranged in the operation section 12 of the endoscope 10 or in the treatment tool 20.

Variations of First Embodiment

Next, endoscope systems 1A to 1F, and the like as variations 1 to 7 of the first embodiment will be described. Since the endoscope systems 1A to 1F, and the like comprise the same components as the endoscope system 1 already described and are similar to the endoscope system 1, the same reference numerals are given to components having the same functions to omit the description thereof.

All the endoscope systems 1A to 1F, and the like have the effects of the endoscope system 1, and further have more beneficial effects than the endoscope system 1, respectively.

<Variation 1> Resonance Circuit

Figure 7:
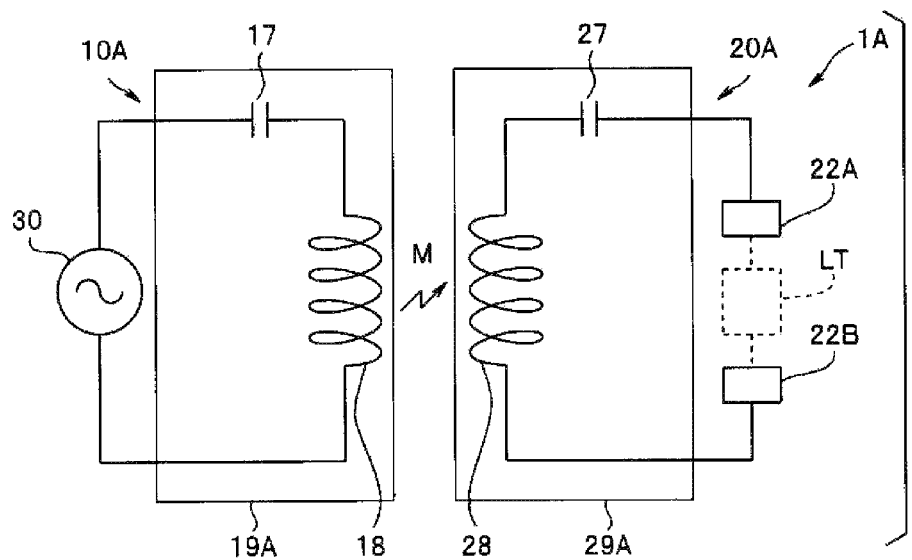
FIG. 7 is an equivalent circuit diagram of an endoscope system as a variation 1 of the first embodiment.

In an endoscope system 1A illustrated in FIG. 7, a power transmission unit 19A of an endoscope 10A and a power reception unit 29A of a treatment tool 20A comprise capacitance elements 17 and 27, respectively. The addition of capacitance components to respective circuits of the power transmission unit 19A and the power reception unit 29A causes the respective circuits to form resonance circuits having predetermined resonant frequencies, respectively. Although it is not impossible to form each resonance circuit only from parasitic capacitance in the circuit, the capacitance element 17, 27 is required to set the resonant frequency to a predetermined value. Further, the capacitance elements 17 and 27 are connected in series with respect to the output of the power source 30 in FIG. 7, but they may be connected in parallel.

Here, the endoscope side circuit comprising the power source 30 and the power transmission unit 19A, and the treatment tool side circuit comprising a power reception unit 29A and a treatment unit 22 (22A, 22B) to apply current to a body tissue LT as a load section that consumes power are separate circuits that do not share the ground.

Then, capacitance C1 of capacitance element 17 of the power transmission unit 19A and inductance L1 of the first coil 18, capacitance C2 of the capacitance element 27 of the power reception unit 29A and inductance L2 of the second coil 28, and a frequency F0 of high-frequency power output from the power source 30 have the following relation (Equation 1).

$$\sqrt{L_{total} \cdot C_{total}} = 1/2\pi F1 = 1/2\pi F0 \quad \text{(Eq. 1)}$$

In other words, the frequency F0 of the high-frequency power output from the power source 30 and a resonant frequency F1 of the power transmission unit 19A are substantially coincide with each other. Therefore, the power transmission unit 19A can generate the AC magnetic field M efficiently. Further, the resonant frequency F1 of the power transmission unit 19A substantially coincides with a resonant frequency F2 of the power reception unit 29A as well. Therefore, since the power transmission unit 19A and the power reception unit 29A become a magnetic-field resonance state, the power reception unit 29A can receive the AC magnetic field M efficiently.

As described above, in the endoscope system 1A, the power transmission unit 19A comprising the transmission coil 18 and the power reception unit 29A comprising the reception coil 28 form respective resonance circuits, where the frequency F0 of the high-frequency power, the resonant frequency of the power transmission unit 19A, and the resonant frequency of the power reception unit 29A are the same. Note that the same frequency means that the frequencies fall within a range of ±5%. The above resonance circuits are designed to comprise, as components thereof, parasitic capacitance and self-inductance generated inevitably due to the wiring structure and the like. In the above description, although the capacitance element 17 is a component of the endoscope 10A, it may be arranged, for example, in the processor 32 because the resonance circuit having the resonant frequency F1 has only to be formed over the entire power transmission unit 19A.

Thus, the transmission/reception efficiency of the endoscope system 1A is higher than that of the endoscope system 1.

<Variation 2> Impedance Matching

Figure 8:
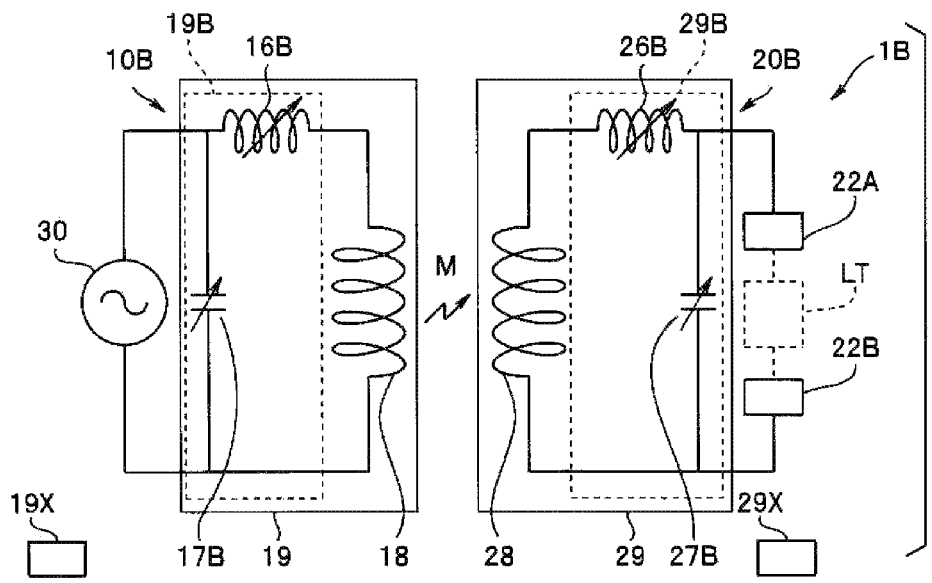
FIG. 8 is an equivalent circuit diagram of an endoscope system as a variation 2 of the first embodiment.

In an endoscope system 1B illustrated in FIG. 8, the power transmission unit 19 and the power reception unit 29 comprise impedance matching units 19B and 29B, respectively.

The impedance matching unit 19B on the side of the power transmission unit 19 comprises an inductance element 16B connected in series and a capacitance element 17B connected in parallel with respect to the output of the power source 30. The impedance matching unit 19B matches the impedance of the power source 30 to a side of the impedance matching unit 19B near the treatment unit 22. Since the impedance is matched, the efficiency of power input from the power source 30 to the treatment unit 22 is high.

On the other hand, the impedance matching unit 29B on the side of the power reception unit 29 comprises an inductance element 26B connected in series and a capacitance element 27B connected in parallel with respect to the treatment unit 22. The impedance matching unit 29B matches impedance on a side of the impedance matching unit 29B near the power source 30 to the impedance of the treatment unit 22. Since the impedance is matched, the efficiency of power input from the side of the impedance matching unit 29B near the power source 30 to the treatment unit 22 is high.

The impedance matching unit 19B of the power transmission unit 19 may comprise a capacitance element 17B connected in series and an inductance element 16B connected in parallel with respect to the output of the power source 30. The impedance matching unit 29B of the power reception unit 29 may comprise a capacitance element 27B connected in series and an inductance element 26B connected in parallel with respect to the treatment unit 22.

In the above description, the inductance element and the capacitance element are used as each impedance matching unit. Although a resistance element such as a resistor, a transmission line, and the like can be combined, it is preferred not to use them because the resistance element increases loss.

In the above description, the impedance matching units 19B and 29B form respective parts of the power transmission unit 19 and the power reception unit 29, but the impedance matching unit 19B may be, for example, part of the processor 32. Further, the impedance matching unit 29B may be arranged in the operation section 21C of a treatment tool 20B. In other words, the structure only has to be designed such that an endoscope 10B comprises the impedance matching unit 19B and the treatment tool 20B comprises the impedance matching unit 29B.

The input endoscope system 1B has higher efficiency of power input from the power source 30 to the power transmission unit 19 than the endoscope systems 1 and 1A.

Both the resonance circuit and the impedance matching circuit of the variation 1 and the variation 2 are components for improving the transmission/reception efficiency of the endoscope system 1, and not essential components. Therefore, only either the endoscope 10 or the treatment tool 20 may comprise at least either of the resonance circuit and the impedance matching circuit, or both may not have the resonance circuit and the impedance matching circuit.

Further, it is preferred that the power transmission unit 19 or the power reception unit 29 should automatically change the reactance of the capacitance element 17B, 27B or inductance element 16B, 26B to achieve the highest transmission/reception efficiency. To this end, as illustrated in FIG. 8, it is preferred that the capacitance elements 17B and 27B be variable capacitance elements and the inductance elements 16B and 26B be variable inductance elements. Note that the variable capacitance elements 17B, 27B and the inductance elements 16B, 26B are controlled by control units 19X, 29X, respectively. The control unit 19X is, for example, arranged in the processor 32, the power source 30, or the endoscope 10B, and the control unit 29X is arranged in the treatment tool 20B.

<Variation 3> Structure of Inductance Element

In the endoscope system 1, the solenoid coils 18 and 28 are taken as an example of the inductance element for generating a magnetic field in the power transmission unit 19 and the inductance element for receiving power in the power reception unit 29, but the inductance elements for generating and receiving the AC magnetic field M are not limited to the solenoid coils.

For example, inductance elements illustrated in FIG. 9A to FIG. 9G can be used. In the drawings, the direction of extending linear conducting wires is the longitudinal direction of the channel 14 or the treatment tool 20.

Figure 9A:
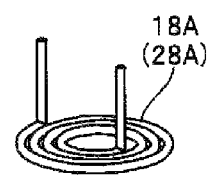
FIG. 9A is a schematic diagram of an inductance element in an endoscope system as a variation 3 of the first embodiment.
Figure 9B:
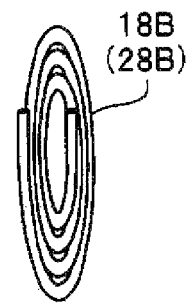
FIG. 9B is a schematic diagram of an inductance element in the endoscope system as the variation 3 of the first embodiment.
Figure 9C:
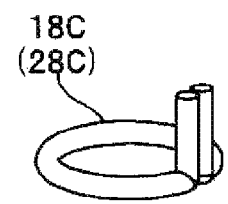
FIG. 9C is a schematic diagram of an inductance element in the endoscope system as the variation 3 of the first embodiment.
Figure 9D:
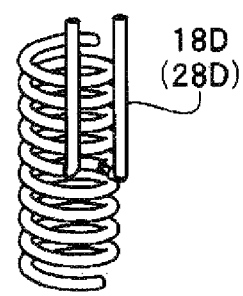
FIG. 9D is a schematic diagram of an inductance element in the endoscope system as the variation 3 of the first embodiment.
Figure 9E:
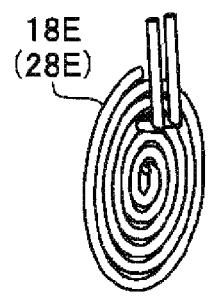
FIG. 9E is a schematic diagram of an inductance element in the endoscope system as the variation 3 of the first embodiment.
Figure 9F:
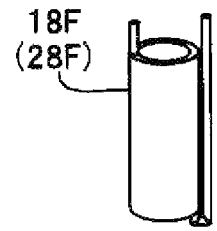
FIG. 9F is a schematic diagram of an inductance element in the endoscope system as the variation 3 of the first embodiment.

A spiral coil 18A (28A) illustrated in FIG. 9A, a spiral coil 18B (28B) illustrated in FIG. 9B to be arranged in the longitudinal direction of the channel 14, a one-turn loop coil 18C (28C) illustrated in FIG. 9C, a solenoid coil 18D (28D) with both ends open as illustrated in FIG. 9D, a spiral coil 18E (28E) with both ends open as illustrated in FIG. 9E, and a hollow cylindrical conductor 18F (28F) illustrated in FIG. 9F can be used. Further, even any simple line (not illustrated) can be used as an inductance element.

The distribution of a generated AC magnetic field, a magnetic field coupling state, and the like greatly vary depending on the structure of the inductance element. However, in any case, since an induced electromotive force is generated in the power reception unit 29 by an AC magnetic field M generated in the power transmission unit 19, power can be wirelessly transmitted.

Figure 9G:
FIG. 9G is a schematic diagram of an inductance element in the endoscope system as the variation 3 of the first embodiment.

The number of inductance elements does not necessarily one. As illustrated in FIG. 9G, it may be made up of two or more inductance elements. Further, the two or more inductance elements may be arranged not only in the longitudinal direction of the channel, but also in the circumferential direction of the channel.

Even when there are multiple patterns in terms of the directivity of the magnetic field M generated by the treatment tool 20 from the inductance element in the power reception unit 29, power can be wirelessly supplied to the treatment tool 20 by arranging multiple inductance elements in the power transmission unit 19 and driving an inductance element appropriate for the treatment tool 20.

As described above, if the inductance element of the power transmission unit 19 and the inductance element of the power reception unit 29 are inductively coupled to each other even a little when they approach each other, the Q value of the resonance circuit comprising the power transmission unit 19 or the power reception unit 29 can be increased even with a small coupling coefficient to make possible wireless power transmission. Note that the structure of the inductance element of the power reception unit 29 may be the same as or different from the inductance element of the power transmission unit 19.

<Variation 4> Relay Structure

Figure 10:
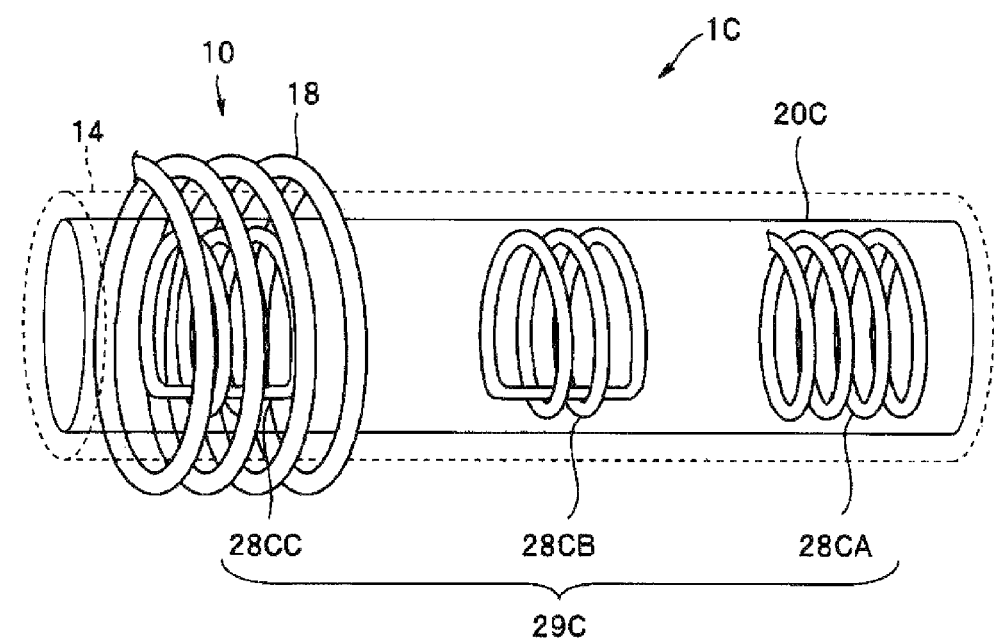
FIG. 10 is a schematic diagram of power transmission/reception units in an endoscope system as a variation 4 of the first embodiment.
Figure 11:
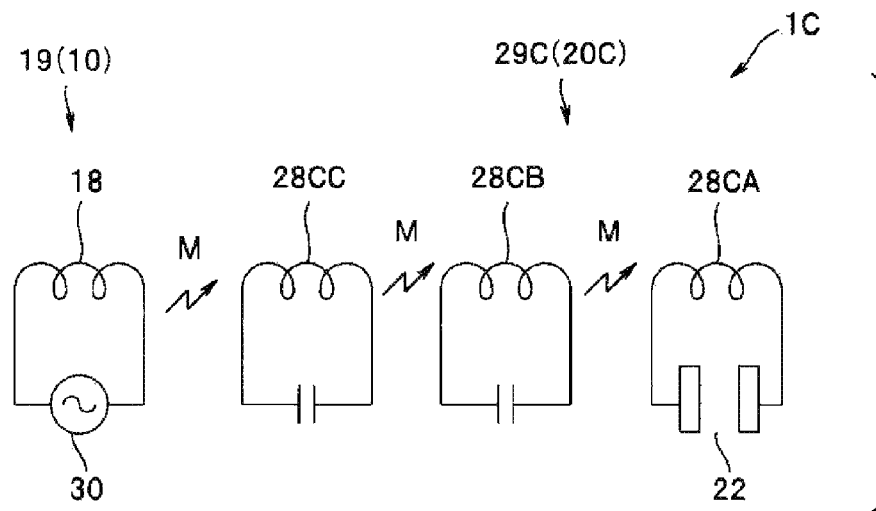
FIG. 11 is an equivalent circuit diagram of an endoscope system as a variation 5 of the first embodiment.

As illustrated in FIG. 10 and FIG. 11, in a treatment tool 20C of an endoscope system 10, a power reception unit 29C comprises a relay coil group. In other words, the power reception unit 29C has a relay coil group composed of multiple relay coil portions 28CB and 28CC, each of which is not electrically connected to any other coil, as well as a reception coil 28CA connected to the treatment unit 22. Note that the number of relay coil portions may be one or more than three.

Each of the relay coil portions 28CB and 28CC is composed of an inductance element (coil) and a capacitance element connected in series. The capacitance element comprises capacitance enough to cancel impedance components of the inductance element.

The transmission coil 18 of the power transmission unit 19 generates an AC magnetic field M by AC power output from the power source 30. The AC magnetic field M generates an induced electromotive force in the relay coil portion 28CC strongly coupled to the transmission coil 18. As a result, the relay coil portions 28CC as a power reception unit with no load connected functions as a power transmission unit to generate an AC magnetic field M. This leads to generating an induced electromotive force in the adjacent relay coil portion 28CB. Likewise, an induced electromotive force is generated in the reception coil 28CA through the relay coil portions 28CB to supply power to the treatment unit 22.

For example, in an endoscope system comprising multiple endoscopes different in channel length D and a treatment tool 20 comprising one reception coil 28, a transmission coil 18 in each of the endoscopes needs to be arranged in a position a predetermined distance D1 from the distal opening 14B as already described.

On the other hand, the treatment tool 20C can wirelessly feed power efficiently if at least any of the reception coil 28CA and the relay coil portions 28CB, 28CC is inserted into the transmission coil 18 and strongly coupled.

Further, when the flexibility of the reception coil 28CA is low, the structure can be such that the reception coil 28CA is arranged in the distal end portion 11A of the channel 14 as an inflexible portion and highly flexible relay coils are arranged in the soft portion 11C to ensure the flexibility of the endoscope insertion section 11. This arrangement of the relay coils in the soft portion 11C can ensure the flexibility of the endoscope insertion section 11 compared with the case of using the long reception coil 28CA. Note that even a relay coil having low flexibility can ensure the flexibility of the endoscope insertion section 11 if the length thereof is short.

In FIG. 10 and the like, the center line of the reception coil 28CA and the relay coil portions 28CB, 28CC is arranged on one straight line, but the center line of these coils may of course be arranged on a curved line as long as they are coaxial.

As described above, in the endoscope system 10, the relay portions (relay coil portions) relaying the AC magnetic field M in the power reception unit 29 of the treatment tool 20 are provided in a row arrangement in the longitudinal direction, and the relay portions and the reception coil 28CA of the power reception unit 29 are not connected by wire. Note that the transmission coil 18 of the power transmission unit 19 may relay the AC magnetic field M through a relay coil group.

It goes without saying that a transmission coil and a reception coil each composed of a coil group comprising multiple coils connected by a conducting wire instead of the relay coil portions have the same effects as those in the endoscope system 1C.

<Variation 5> Shielding Member

Figure 12:
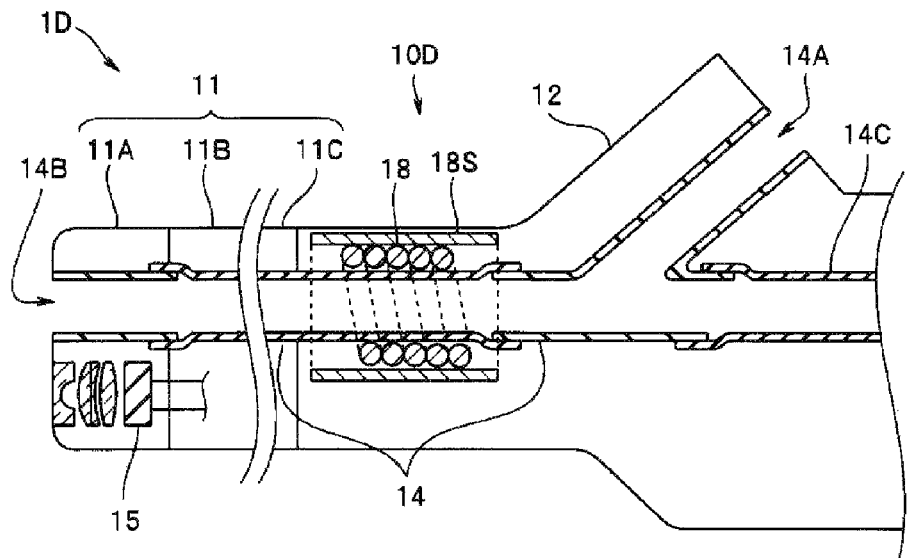
FIG. 12 is a schematic sectional view of an endoscope in an endoscope system as a variation 6 of the first embodiment.

In the endoscope system 1, since the power transmission unit 19 is arranged inside the endoscope 10 as already described, a generated electromagnetic field M is less likely to leak outside the endoscope 10. In order to prevent a further leakage electromagnetic field, an endoscope system 1D comprising an endoscope 10D with a shielding member 18S arranged therein to shield an electromagnetic field Mas illustrated in FIG. 12 is preferable. Although the shielding member 18S only needs to be arranged to cover at least part of the outer circumference of the first coil 18, it is preferred that shielding member 18S should be arranged to cover the outer circumference completely.

As the shielding member 18S, a conductive material, for example, a metal material such as gold, silver, copper, aluminum, or stainless steel, highly doped semiconductor, conductive resin, or the like is used. Note that use of a soft magnetic material such as Permalloy as the shielding member allows the shielding member to obtain not only the shielding effect, but also an effect as a magnetic yoke for controlling the path of magnetic lines and the effect of increasing the coupling coefficient of coils thereby. Here, the shielding member 18S may be connected to the ground (ground-connected).

It is also preferred to use a stack of a conductive material and a magnetic material as the shielding member 18S. In this case, the conductive material is arranged on the outer side of the magnetic material to narrow the expansion of the magnetic field M by the effect of the magnetic yoke of the magnetic material, and this can reduce the magnetic field M entering the conductive material and hence the eddy loss to prevent a reduction in transmission efficiency.

As described above, the channel 14 is covered with the shielding member 18S covering the power transmission unit 19 in the endoscope system 1D. Then, the shielding member 18S is either a conducting body or a magnetic body. Alternatively, when the shielding member 18S is composed of the conducting body and the magnetic body, it is preferred that the conducting body be arranged in a more outer circumference than the magnetic body.

Note that a magnetic core made of a soft magnetic material may be inserted into the second coil 29 of the treatment tool 20.

<Variation 6> Treatment Tool

As devices inserted into the channel 14 of the endoscope 10 in the endoscope system 1, various bipolar treatment tools, each comprising a load section operating with power received by the power reception unit 29, can be used. In other word, for example, high-frequency incision forceps, high-frequency hemostatic forceps, hot biopsy forceps, a high-frequency coagulation treatment tool, an AC generating treatment tool for plasma, a heating treatment tool, a cooling treatment tool, a vibrating treatment tool, a radiation treatment tool, or the like can be used as the treatment tool 20.

Further, the devices are not limited to treatment tools for applying high-frequency power to the body tissue LT to do treatments, and the devices may also be various electric-driven treatment tools. For example, the endoscope system can be used for an ultrasonic treatment tool using ultrasonic vibration to make an incision in a body tissue and coagulate the body tissue, an ultrasonic suction treatment tool using ultrasonic vibration to grind and suck a body tissue, a resection treatment tool using a turning force of a drill or the like to grind a body tissue, a treatment tool with an actuator having the function of electrically driving the tips of forceps, and the like.

Further, even a device such as a probe, which is passed through the channel 14 but the distal end portion 21A thereof does not protrude from the distal opening 14B, can output wirelessly transmitted power to the load section in the same manner as the treatment tool 20. In other words, the devices in the present invention comprise a probe and the like that are passed through the channel 14 but the distal end portion 21A thereof does not protrude from the distal opening 14B.

For example, even a probe comprising multiple magnetism generating elements of an endoscope shape detector for detecting an endoscope insertion shape is a device of the present invention. Power received through wireless transmission is output to the magnetism generating elements as a load section.

Figure 13:
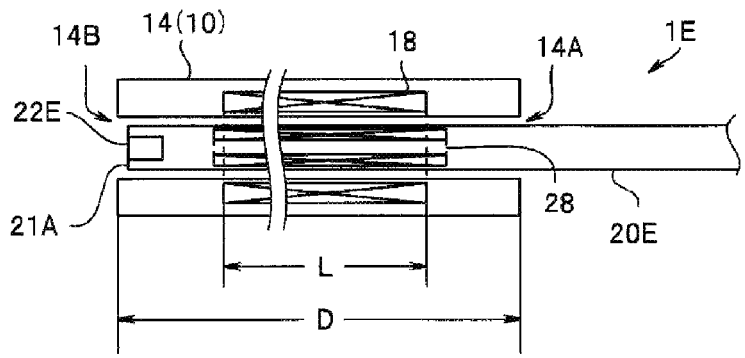
FIG. 13 is a schematic sectional view of an endoscope system as a variation 7 of the first embodiment.

Further, as illustrated in FIG. 13, an auxiliary light probe 20E with an LED element 22E arranged in a distal end portion thereof in an endoscope system 1E is also used in a state where the distal end portion 21A does not protrude from the distal opening 14B. The received power is output to the LED element 22E as a load section.

As illustrated in FIG. 13, even in the case of the auxiliary light probe 20E whose distal end portion 21A does not protrude from the distal opening 14B, the power reception unit 29 is arranged in a position of receiving the AC magnetic field M generated by the power transmission unit 19 most efficiently in a state of being inserted into the channel 14 up to the operating position, i.e., in an inserted state where the supply of power is required.

When the auxiliary light probe 20E is used, for example, even an endoscope having no special light observation function can irradiate, if needed, an affected area with special light of a wavelength appropriate to the affected area and generated by the auxiliary light probe 20E to make more effective observations.

In an endoscope system comprising multiple treatment tools different in required power, since the output of the power source 30 needs to be adjusted according to the load of each of the treatment tools, the operation is complicated. Therefore, it is preferred that the endoscope system should comprise treatment tools each with power reception efficiency corresponding to the load.

For example, the number of turns of the second coil 28 is set small for a treatment tool for which a power of 1 W is required so that the power reception efficiency of the treatment tool will be 1/100 of the power reception efficiency of a treatment tool for which a power of 100 W is required.

In other words, in an endoscope system comprising multiple treatment tools, a treatment tool with lower power required for the treatment is so set that the power transmission efficiency between the power transmission unit 19 and the power reception unit 29 will be reduced.

Since an endoscope system comprising multiple treatment tools, each comprising a power reception unit the power reception efficiency of which is set according to each load, does not need to adjust the output of the power source 30 according to the treatment tool 20, the operability is good.

<Variation 7> Power Conversion

In the endoscope system 1 and the like, high-frequency AC power received by the power reception unit 29 is used directly for a treatment through the treatment unit 22. In other words, the power used for the treatment is the same as the high-frequency power output from the power source 30, for example, a sinusoidal AC power of 13.56 MHz.

Figure 14:
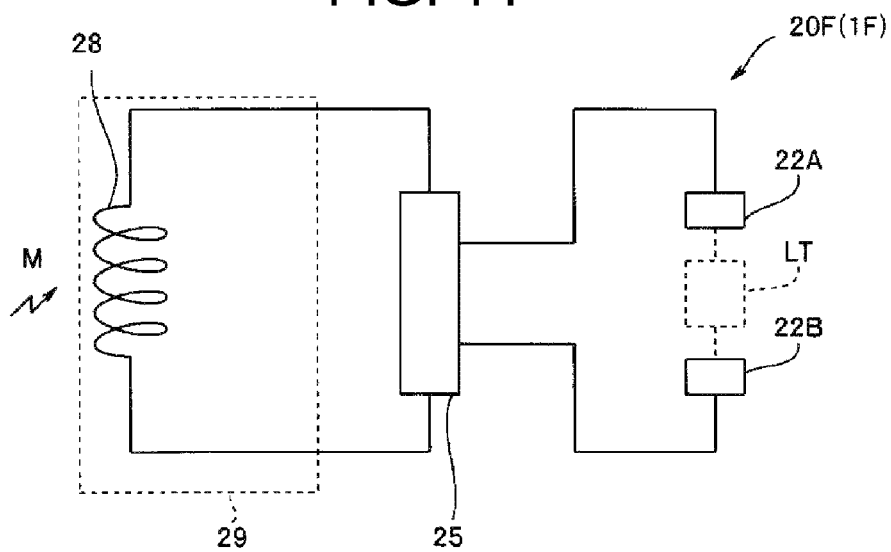
FIG. 14 is a configuration diagram of an endoscope system as a variation 8 of the first embodiment.

On the other hand, as illustrated in FIG. 14, a treatment tool 20F in an endoscope system 1F comprises a power conversion unit 25 for converting high-frequency power received by the power reception unit 29 and outputting the covered power to the treatment unit 22. The power conversion unit 25 converts the power, received by the power reception unit 29, to power appropriate for a treatment through the treatment unit 22. Further, though not illustrated, the treatment tool 20F in the endoscope system 1F may also comprise an output switching unit as a switch for switching between outputting the high-frequency power, received by the power reception unit 29, directly to the treatment unit 22, and outputting the high-frequency power to the power conversion unit 25.

For example, the power conversion unit 25 modulates the amplitude or frequency of sinusoidal, high-frequency AC power to obtain DC power, pulse waveform power, attenuation waveform power, square-wave power, or the like.

As described above, the treatment tool 20F in the endoscope system 1F comprises the power conversion unit 25 for converting the waveform or the like of the power received by the power reception unit 29 into a waveform or the like of power to be applied by the treatment unit. Further, the treatment tool 20F comprises the output switching unit for applying, to the treatment unit 22, either the power received by the power reception unit 29 directly or power converted by the power conversion unit 25.

The endoscope system 1F for converting the power, received by the power reception unit 29, into power appropriate for a treatment and outputting the converted power to the treatment unit 22 can do a better treatment.

Second Embodiment

Next, an endoscope system 1G of a second embodiment will be described. Since the endoscope system 1G is similar to the endoscope systems 1 to 1F already described, the same reference numerals are given to components having the same functions to omit the description thereof.

Figure 15:
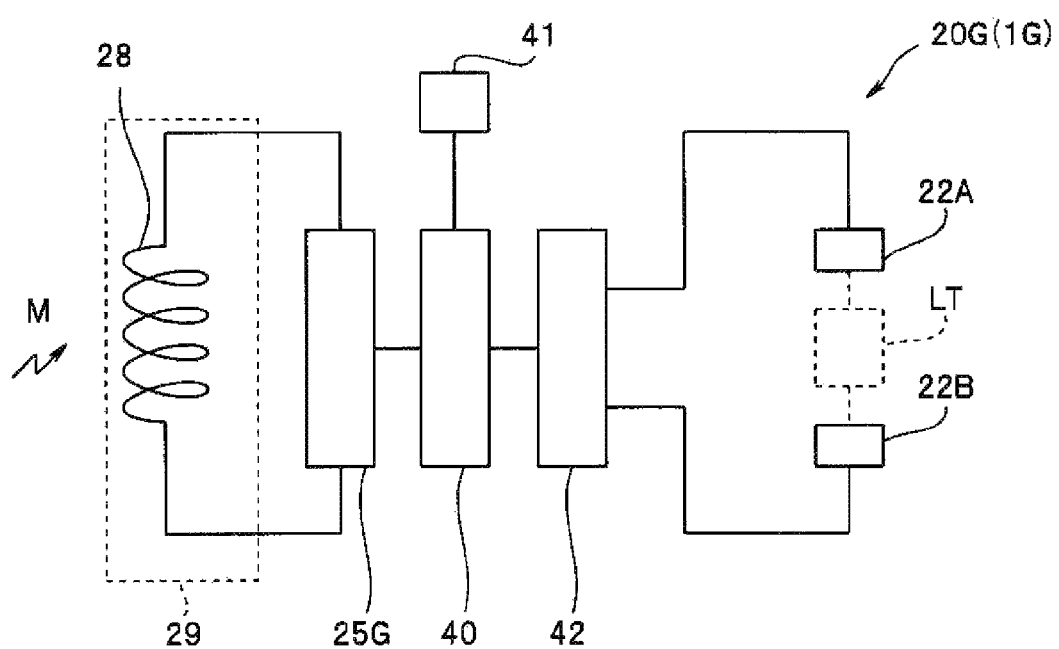
FIG. 15 is a configuration diagram of an endoscope system of a second embodiment.

As illustrated in FIG. 15, a treatment tool 20G in the endoscope system 1G comprises a power conversion unit 25G for converting received AC power to DC power, a power storage unit 40 for storing power output from the power conversion unit 25G, a notice unit 41 for giving notice of a power storage state of the power storage unit 40, and a drive unit 42 for converting the DC power stored in and output from the power storage unit 40 into power according to the specification of the treatment unit 22.

The power storage unit 40 is not limited to a battery such as a lithium-ion secondary battery. For example, an electric double layer capacitor can be used particularly preferably as the power storage unit 40 because it can be charged and discharged rapidly with little degradation of capacity caused by charging and discharging, though the power storable capacity is smaller than the secondary battery. Further, the power storage unit 40 may be composed of the secondary battery and the electric double layer capacitor.

The notice unit 41 is an indication unit made up, for example, of an LED to indicate the amount of power storage (remaining power level) of the power storage unit 40. For example, the indication unit glows green when the amount of power storage is enough to allow a prolonged treatment, glows yellow when the amount of power storage is a bit small, and glows red when the amount of power storage is too small to do the treatment. Further, when the power storage unit 40 electrically discharged for the treatment stores the received power and the amount of power storage becomes enough for a treatment, the notice unit 41 may generate sound, light, vibration, or the like to notify the operator of that effect.

The endoscope system 1G comprises the effects of the endoscope system 1 and the like, and further can do a treatment in a state where the power reception unit 29 cannot receive power. Although an endoscope system comprising a primary battery can obtain the above effect, it is more preferred to comprise the power storage unit 40 without a need to exchange batteries.

The time required for the treatment unit 22 to use power is short and intermittent. Therefore, even if the power reception unit 29 can receive only low power, the treatment tool 20G can charge the power storage unit 40 during an interval between treatments.

Further, in a treatment tool using received power directly for a treatment, when the amount of power required for the treatment is large, there is a need to increase the strength of a magnetic field generated by the power transmission unit 19. However, there is a limit on the magnetic field strength capable of being generated by the power transmission unit 19, that is, on the power capable of being supplied directly to the treatment unit 22.

Since the treatment tool 20G uses, for a treatment, power stored in the power storage unit 40, there is no problem if the power required by the treatment unit 22 exceeds the power received by the power reception unit 29, and a high-power treatment can be done despite the generation of a strong magnetic field being unnecessary. In other words, the power transmission unit 19 does not need to generate a strong magnetic field M even when high power is required instantaneously. Therefore, there is no danger to cause adverse effects of a leakage electromagnetic field on peripheral devices.

In other words, since the high-frequency power output from the power source 30 can be reduced in the endoscope system 1G, the magnetic field leakage from the power transmission unit 19 is reduced, and it is less likely to cause the heat generation problem or the like.

Of course, when power required for a treatment is low, the power received by the power reception unit 29 may be used directly for the treatment even in the endoscope system 1G.

Here, endoscope systems obtained by combining the aforementioned embodiments and variations have a combination of the effects of respective endoscope systems.

For example, an endoscope system of one embodiment is an endoscope system comprising: a flexible endoscope comprising a flexible insertion section comprising a distal end portion in which an imaging unit is arranged, an operation section arranged on a base end side of the insertion section, and a channel that passes through the insertion section; a power supply for outputting high-frequency power; and a treatment tool with a treatment unit comprising a pair of blades for supplying the high-frequency power to an area to be treated, the treatment unit being inserted from an insertion opening of the operation section and protruding from an opening of the distal end portion through the channel, wherein the endoscope comprises a power transmission unit comprising a first solenoid coil wound around an outer circumference of the channel and covered with a shielding member for shielding an electromagnetic field to generate an AC magnetic field by the high-frequency power input from the power source so as to form a first resonance circuit comprising a resonant frequency identical to the frequency of the high-frequency power, and the treatment tool comprises: a power reception unit comprising a second solenoid coil that penetrates through the first solenoid coil in a state where the treatment unit protrudes from the opening to form a second resonance circuit comprising a resonant frequency identical to that of the first resonance circuit; a power storage unit for storing power received by the power reception unit and outputting, to the treatment unit, power higher than the power received by the power reception unit; and a notice unit for giving notice of a power storage state of the power storage unit.

The present invention is not limited to the aforementioned embodiments, variations, and the like, and various changes, combinations, and applications are possible without departing from the spirit of the invention.

The invention claimed is:

1. An endoscope system comprising:
an endoscope comprising:
   an endoscope insertion section comprising a portion that is flexible, wherein the endoscope defines a channel having a distal opening in the endoscope insertion section; and
   a first inductance element arranged to the channel, wherein the first inductance element is configured to receive a high-frequency power from a power source to generate an AC magnetic field; and
a treatment tool comprising:
   a treatment tool insertion section configured to be movably inserted in the channel of the endoscope;
   an electrically powered treatment device attached to the treatment tool insertion section to be moved by the treatment tool insertion section;
   a second inductance element arranged to the treatment tool insertion section, wherein the second inductance element is inductively coupled to the first inductance element such that the AC magnetic field induces an electromotive force to generate an induced current in the second inductance element; and
   a power converter configured to convert power received by the second inductance element to power used by the electrically powered treatment device to perform a treatment, and to directly or indirectly output the converted power to the treatment device to power the electrically powered treatment device to perform the treatment.

2. The endoscope system according to claim 1,
wherein the first inductance element and the second inductance element are configured to form resonance circuits, and
wherein the resonance circuits have a resonant frequency that coincides with a frequency of the high-frequency power.

3. The endoscope system according to claim 1,
wherein the first inductance element comprises a first coil extending in a longitudinal direction of the channel of the endoscope, and wherein the second inductance element comprises a second coil extending in a longitudinal direction of the treatment tool insertion section.

4. The endoscope system according to claim 1,
wherein in an inserted state of the treatment tool, the treatment tool insertion section is inserted in the channel of the endoscope to protrude the electrically powered treatment device from the distal opening in the endoscope insertion section, and
wherein in the inserted state, the second inductance element is inductively coupled to the first inductance element.

5. The endoscope system according to claim 1,
wherein the electrically powered treatment device comprises a pair of blades for supplying the power output by the power converter to an area to be treated.

6. The endoscope system according to claim 1,
wherein the treatment tool further comprises a power storage device configured to store the power output by the power converter and to output the stored power directly or indirectly to the electrically powered treatment device.

7. The endoscope system according to claim 6,
wherein the treatment tool further comprises a display configured to display a power storage state of the power storage device.

8. The endoscope system according to claim 6,
wherein the power output by the power storage device is higher than the power received by the second inductance element.

9. The endoscope system according to claim 1,
wherein the treatment tool further comprises a spiral coil arranged in the treatment tool insertion section to provide the treatment tool insertion section with flexibility and mechanical strength, and
wherein the second inductance element is formed from a part of the spiral coil.

10. An endoscope system comprising:
an endoscope comprising:
    an endoscope insertion section comprising a portion that is flexible, wherein the endoscope defines a channel having a distal opening in the endoscope insertion section; and
    a first inductance element arranged to the channel, wherein the first inductance element is configured to receive a high-frequency power from a power source to generate an AC magnetic field; and
a treatment tool comprising:
    a treatment tool insertion section configured to be movably inserted in the channel of the endoscope;
    an electrically powered treatment device attached to the treatment tool insertion section to be moved by the treatment tool insertion section;
    a second inductance element arranged to the treatment tool insertion section, wherein the second inductance element is inductively coupled to the first inductance element such that the AC magnetic field induces an electromotive force to generate an induced current in the second inductance element; and
    a power storage device configured to store power received by the second inductance element and to directly or indirectly output the stored power to the electrically powered treatment device to power the electrically powered treatment device to perform a treatment.

11. The endoscope system according to claim 10,
wherein the first inductance element and the second inductance element are configured to form resonance circuits, and
wherein the resonance circuits have a resonant frequency that coincides with a frequency of the high-frequency power.

12. The endoscope system according to claim 10,
wherein the first inductance element comprises a first coil extending in a longitudinal direction of the channel of the endoscope, and
wherein the second inductance element comprises a second coil extending in a longitudinal direction of the treatment tool insertion section.

13. The endoscope system according to claim 10,
wherein in an inserted state of the treatment tool, the treatment tool insertion section is inserted in the channel of the endoscope to protrude the electrically powered treatment device from the distal opening in the endoscope insertion section, and
wherein in the inserted state, the second inductance element is inductively coupled to the first inductance element.

14. The endoscope system according to claim 10,
wherein the electrically powered treatment device comprises a pair of blades configured to supply the power output by the power storage device to an area to be treated.

15. The endoscope system according to claim 10,
wherein the treatment tool further comprises a power converter configured to convert the power received by the second inductance element to power used by the electrically powered treatment device to perform the treatment, and to output the converted power to the power storage device for storage.

16. The endoscope system according to claim 10,
wherein the treatment tool further comprises a display configured to display a power storage state of the power storage device.

17. The endoscope system according to claim 10,
wherein the stored power output by the power storage device is higher than the power received by the second inductance element.

18. The endoscope system according to claim 10,
wherein the treatment tool further comprises a spiral coil arranged in the treatment tool insertion section to provide the treatment tool insertion section with flexibility and mechanical strength, and
wherein the second inductance element is formed from a part of the spiral coil.

* * * * *